United States Patent [19]

Dow et al.

[11] Patent Number: 4,913,155

[45] Date of Patent: Apr. 3, 1990

[54] ULTRASONIC TRANSDUCER PROBE ASSEMBLY

[75] Inventors: Julian Dow, San Clemente; Paul F. Meyers, San Juan Capistrano, both of Calif.

[73] Assignee: Capistrano Labs, Inc., San Clemente, Calif.

[21] Appl. No.: 267,110

[22] Filed: Oct. 24, 1988

Related U.S. Application Data

[63] Continuation of Ser. No. 47,479, May 11, 1987, abandoned.

[51] Int. Cl.[4] .................... A61B 8/00

[52] U.S. Cl. .................... 128/660.1; 73/634

[58] Field of Search .................... 128/660.09, 660.10; 73/618–620, 633–634

[56] References Cited

U.S. PATENT DOCUMENTS

| | | | |
|---|---|---|---|
| 3,955,561 | 5/1976 | Eggleton | 128/661 X |
| 4,092,867 | 6/1978 | Matzuk | 73/609 |
| 4,282,879 | 8/1981 | Kunin et al. | 128/660.09 |
| 4,421,118 | 12/1983 | Dow et al. | 73/620 X |
| 4,545,117 | 10/1985 | Okamoto | 310/314 X |
| 4,785,819 | 11/1988 | Pearce | 128/660.1 |

*Primary Examiner*—Francis Jaworski
*Attorney, Agent, or Firm*—Stetina and Brunda

[57] ABSTRACT

A transducer is pivoted by a linear motor having an electrical coil as the reciprocally moving member. The coil is in a plane orthogonal to the lines of magnetic flux between opposed permanent magnets of opposite polarity affixed to the probe case, providing efficiency. A mechanical linkage between the linear motor electrical coil moving member and the transducer which is forced in pivoting motion transmits only axial force, and not torque, by employing a ball and socket joint at one end of a crankshaft. Electrical connections to the electrical coil are facilitated through springs which additionally mechanically bias the reciprocal movement of the coil. Electrical connections to the pivoting transducer are facilitated through a helical coil wrapping the pivot shaft. These electrical connections accomodate mechanical motions within the probe. A bellows-fold cylindrical air bladder is positioned within the fluid chamber of the probe to allow for thermally-induced changes in fluid volume.

7 Claims, 4 Drawing Sheets

Fig. 1
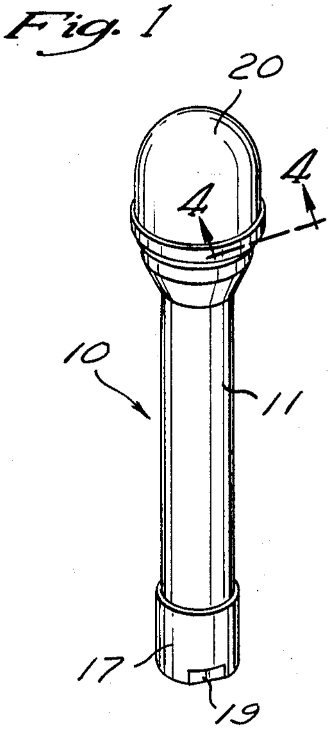
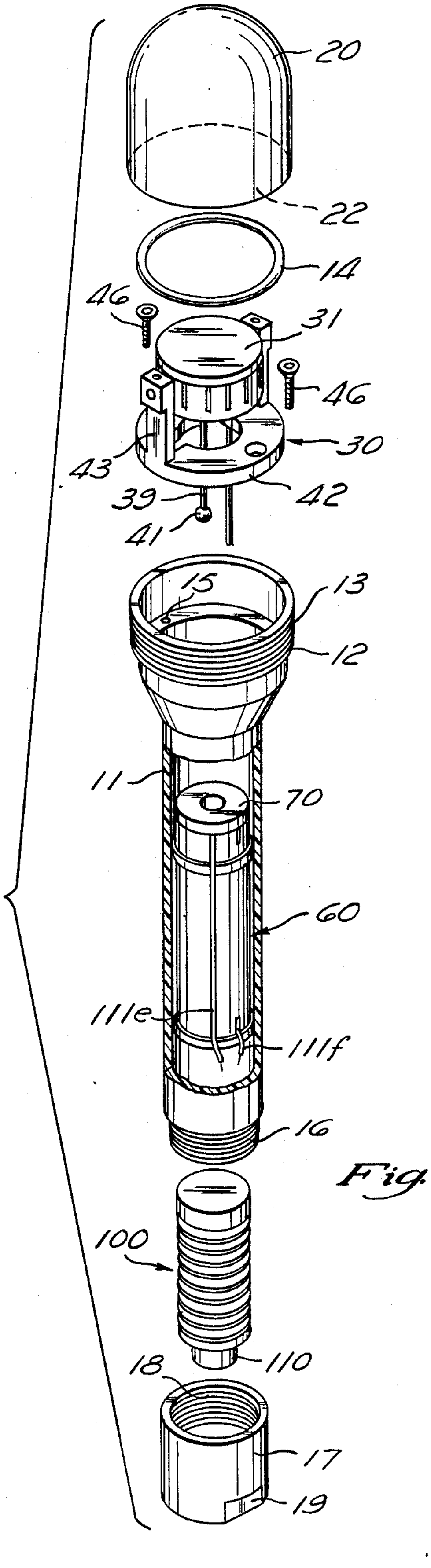
Fig. 2
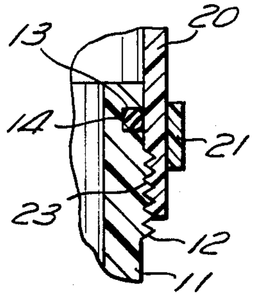
Fig. 4
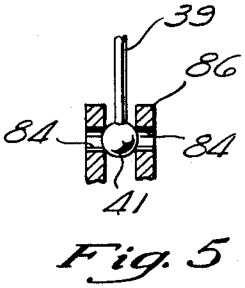
Fig. 5
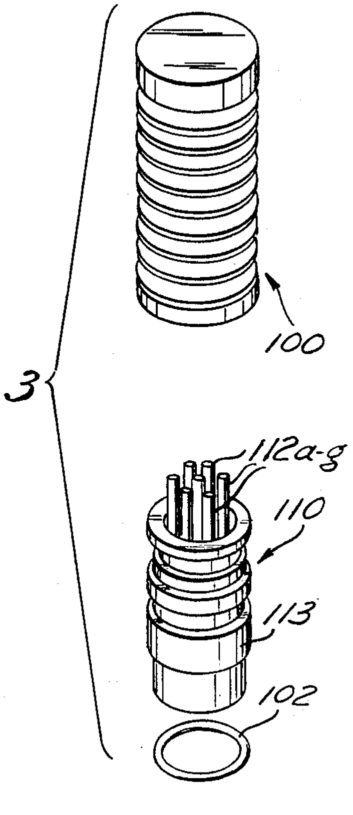
Fig. 3

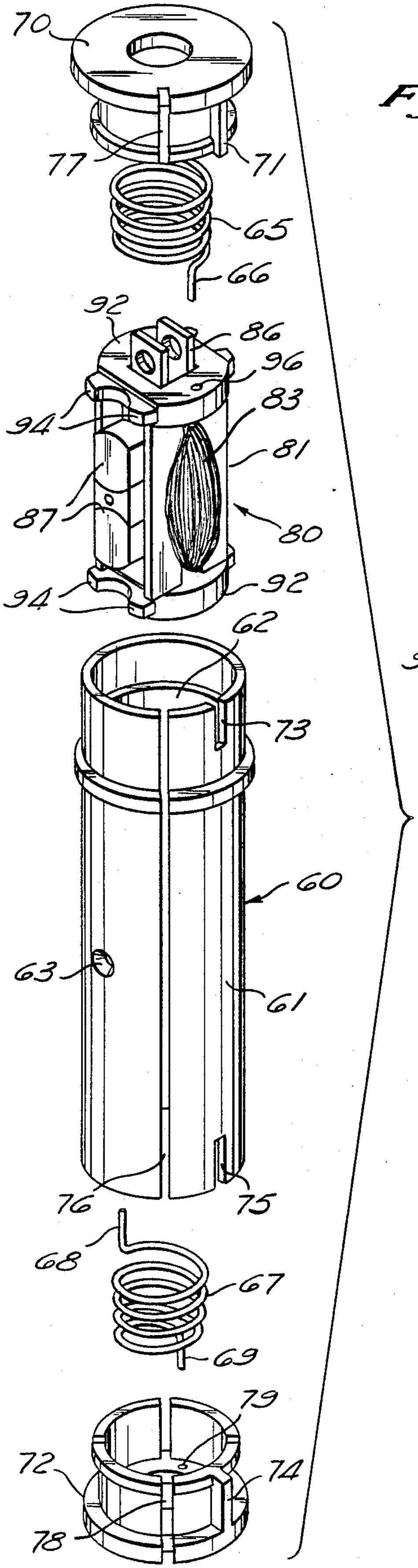
Fig. 10
Fig. 9
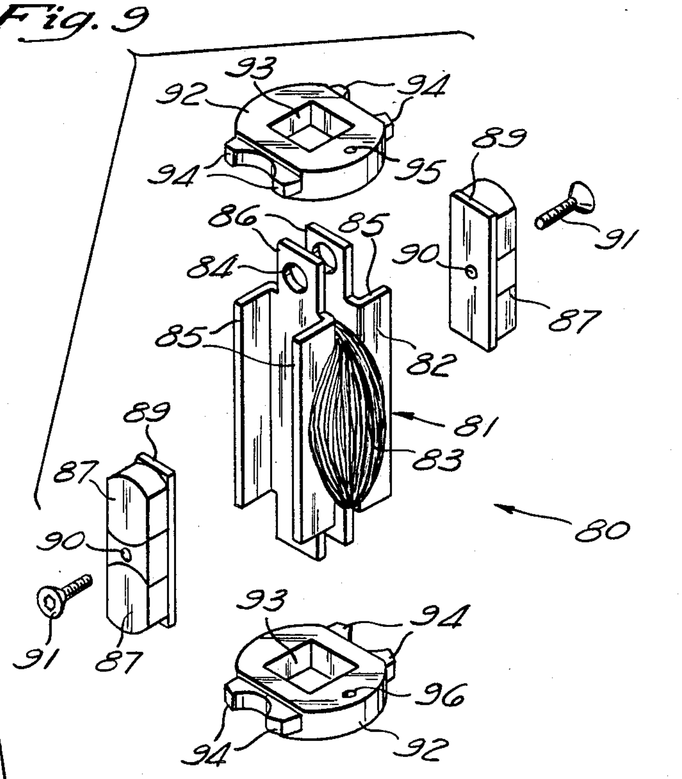
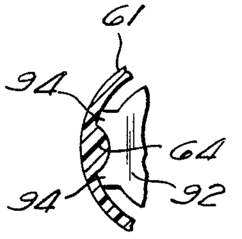
Fig. 11

ULTRASONIC TRANSDUCER PROBE ASSEMBLY

This application is a continuation of application Ser. No. 07/047,479, filed 5/11/87, and now abandoned.

DESCRIPTION OF THE RELEVANT ART

1. Field of the Invention

The present invention concerns an ulrasonic transducer probe assembly for use with a real-time ultrasound diagnostic scanner. More specifically the present invention concerns a novel transducer probe head assembly comprising a linear motor which is connected to a transducer head.

2. Description of the Relevant Art

In the field of ultrasonic diagnostics it is necessary to obtain acoustic images of body tissue. The field of ultrasonic cardiology presents unique problems in that the heart is partially obscured from the ultrasound search and echo signals are caused by costal cartilage and ribs. Therefore, when using the well known sector scan developed for cardiology, it is usually desirable that a transducer probe be used which exhibits a point of rotation of the ultrasound search signal beams (i.e. the region of intersection of the search beams) in front of the transducer probe itself, in the intercostal region.

In order to produce real-time images,, beams of ultrasonic energy must be rapidly transmitted into the patient and echoes received by the probe must be rapidly processed in an image format suitable for display. Desirably, the probe will produce an image over a wide field of view using the sector scan format. A sector scan image is produced by repeatedly transmitting and receiving ultrasonic energy in a number of radial directions from the probe. The ultrasonic beam may be directed either electronically, as by an electronically phased linear array probe, or it may be directed mechanically by a mechanically moving transducer probe.

The subject of the present invention is mechanically moving transducer probes, in which the transducer is physically swept through an arc to produce a sector scan. Such mechanical probes may be advantageously compared with phased array probes when a relatively simple mechanical drive assembly in the mechanical probe is used to perform the same beam steering function as is alternatively performed by the relatively complex electronics used within a phased array probe.

An unltrasonic transducer probe should be physically small in size. Small size allows the user to image at certain body portions with greater ease and reduces user fatigue which occurs with the use of large probes. In a mechanical probe, the mechanism used to move, or oscillate, the transducer should be simple and rugged for ease of manufacturability and reliability. The parts of the probe should be capable of being assembled prrecisely and quickly, without the need for time-consuming or intricate alignment procedures. The finished probe should be capable of withstanding occasional accidental abuse, such as the impact shock of being accidentally dropped. It should be insensitive to normal temperature variations.

A multi-element rotating head transducer has been disclosed in the U.S. Pat. No. 4,149,419, entitled "Ultrasonic Transducer Probe" issued Apr. 17, 1979 to R. Connell, et al. In this multi-element rotating transducer probe the alignment of each piezoelectric element is critical since three or four elements will be used successively to scan a particular organ. Unless the elements are precisely aligned, the images produced on the cathode ray tube screen will jump or be misaligned as the different elements are activated successively when each element assumes its position opposite the organ, i.e. the heart. The single element probe overcomes this disadvantage.

A pivotally mounted ultrasonic transducer head undergoing oscillatory motion has been disclosed in U.S. Pat. No. 3,955,561 entitled "Cardioscan Probe" issued May 17, 1976 to R. Eggleton. This pivotally mounted probe includes a rotating motor within the probe head. The rotating motor and the pivotal motion create vibrations which can be discomforting to the patient. A linear reciprocating motor obviates this disadvantage.

An ultrasonic transducer probe undergoing linear reciprocating motion has been disclosed in U.S. Pat. No. 4,421,118 entitled "Ultrasonic Transducer" issued Dec. 20, 1983 to J. Dow, et al. A compact transducer probe is described which uses a four-bar linkage mechanism to move the transmit-receive transducer crystal through a sector scan angle of up to 90 degrees. A linear reciprocating motor which is coupled to the transducer crystal by means of a crank and drive bar provides the force necessary for the crystal to undergo the scanning motion. By suitably dimensioning the four-bar linkage, the focal point of the scanning beams is located in front of the probe, in the intercostal region, as the crystal undergoes swinging motion.

Within this transducer probe of Dow, et al., the motor comprises a stack of magnets, each magnet being separated from an adjoining magnet by a steel spacer. The magnets are disposed with the same magnetic poles facing each other. Surrounding the stack of magnets is a tubular coil form having a plurality of electrical coils disposed thereon in a manner to cause a respective coil to be located opposite a respective spacer. Adjacent serially connected coils are oppositely wound. When current passes through the coils, a return flux paths through the magnets pushes adjacent coils in the same direction, thereby causing the coil form to move with a force equivalent to the sum of a force of the plurality of coils. By supplying an alternating current signal, the coils undergo a linear reciprocation motion. The tubular coil form is coupled to a crank for causing the transducer crystal to undergo almost circular swinging motion.

Still another ultrasonic transducer probe of the present inventor Dow of the aforementioned U.S. Pat. No. 4,421,118 is pertinent to the present invention. This probe is shown within laid-open European Patent Application No. 86300160.8 claiming a priority date of Jan. 14, 1985 for U.S. patent application Ser. No. 691,319. An improved mechanical transducer probe mechanism is located inside a hollow probe case. A reference point for assembly is located on the inner surface of the case. A motor assembly and a transducer mounting assembly are located within the case and are fixedly joined together. At the jointure of the two, the motor and transducer assemblies are in contact with the reference point, thereby positionally locating the transducer and its drive mechanism within the case. Means are provided for urging the motor and transducer assemblies against the reference point, which means also provide shock mounting for the probe mechanism. Further, the pivoting transducer and its drive mechanisms are contained within a fluid chamber. A portion of the wall of the fluid chamber includes a flexible bellows, which expands and contracts as pressure and temperature changes alter the fluid volume, thereby altering the fluid chamber volume.

Certain disadvantages and limitations are present within the prior implementations of ultrasonic transducer probes undergoing linear reciprocating motion. The linear motors for inducing the reciprocating motion employ a magnet assembly, which is normally of relatively great weight, which moves in the magnetic field of a fixed coil assembly, which is normally of relatively lessor weight. Mechanical oscillatory forces are thuds maximized, and not minimized as is desired. Furthermore, the field lines of magnetic force between the magnet assembly and the coil are not substantially parallel, meaning that the coupling of flux is not optionally efficient to induce motion.

Another disadvantage and limitation exists in the prior art manner of coupling the moving and driving element of the linear motor to the transducer assembly in order to affect reciprocating motion drive of the transducer assembly. This coupling has been by a linkage comprising a crankshaft affixed to a crank pin in a bearing fit. This manner of coupling cannot tolerate either angular rotation, or any significant deviation from an angular alignment, which is of tight tolerance, between the driving (linear motor) and driven (transducer) elements, either upon initial assembly or during use and wear. Although the moving and driven elements cannot rotate relative to each other without binding or breaking the crankshaft drive linkage, they are prone to do so. This causes stalling and even catastrophic failure of the reciprocating transducer motion.

A further disadvantage and limitation of the prior implementations exists regarding the wired electrical coupling and communication which is made to probe elements for powering, actuating, and/or sensing these elements. In the prior art transducer probe assemblies, wired communication has generally been based on extension and takeup bends, loops, coils, lengths of slack wire, and the like. The motion undergone by these wired electrical connections is not only poorly integrated with the mechanical elements for reducing counteracting forces and stresses but may additionally be so poorly accommodative of the mechanical motions within the probe that the electrical interconnections are caused to short or open, causing probe failure.

These and other disadvantages and limitations of the prior implementations of ultrasonic transducer probes are dealt with by the present invention.

SUMMARY OF THE INVENTION

The present invention is embodied in an ultrasonic transducer probe assembly. In accordance with a first aspect of the present invention the preferred embodiment ultrasonic transducer probe head assembly incorporates a linear motor having an electrical coil which is the moving member.

In accordance with a second aspect of the present invention, connection of this moving coil member of the linear motor to a pivoting transducer head is facilitated by a crankshaft. At least one end of the crankshaft has a joint, nominally a ball and socket joint, which is substantially insensitive to angular alignment between the moving coil and pivoting transducer head components.

In accordance with a third aspect of the present invention, the electrical wired communication to all ultrasonic transducer probe assembly elements is integrated with the mechanical motions undergone within the probe assembly. Particularly, the electrical energization of the moving element coil assembly is through the selfsame mechanical springs which mechanically bias the oscillatory movement of such coil assembly. Particularly, the electrical wired communication to the pivoting transducer head assembly is by a wire which wraps the pivot shaft of this pivoting transducer head by a helical coil of several turns.

In accordance with a fourth aspect of the present invention the fluid chamber of the probe assembly completely contains a compressible bladder, nominally in the form of a cylinder with bellows folds along its surface. The bladder allows and compensates for volumetric changes with temperature of fluid contained within the chamber. These four aspects and other aspects of the present invention are directed to the creating of an ultrasonic transducer probe assembly which is simultaneously easy to assemble, smoothly operating, and electrically and mechanically durable.

In accordance with the first aspect of the present invention, the moving coil element of the linear motor moves within a magnetic field which is established by permanent magnets fixed upon the case of the transducer probe asssembly. The electric coil is wound substantially within a plane, and this plane is both positioned within and moving substantially orthogonally to the field lines of magnetic flux created by the permanent magnet. Equivalently, it may be said that the field lines of magnetic flux which are created by electrical energization of the coil are substantially coincident with the field of magnetic flux which are generated by the permanent magnents within which the coil moves. This geometry supports maximum efficiency electromagnetic force coupling.

Moreover in the preferred configuration of the present invention wherein an electrical coil is the moving element of a linear motor and wherein this moving coil also efficiently couples magnetic flux, the linear reciprocating motion of this moving coil is bi-directionally mechanically biased by spring elements located at each end of the coil. In accordance with the third aspect of the present invention, electrical connection to the coil for its energization proceeds directly through these mechanical spring elements, thus simultaneously serving to provide electrical connection as well as imparting mechanical biasing forces.

In accordance with the second aspect of the present invention, one end of the reciprocating coil moving element of the linear motor is mechanically coupled by a linkage to a transducer head which tilts about a pivot axis in order to impart pivoting motion to this transducer head. The pivot axis of the transducer, which is substantially perpendicular to the major axis of the ultrasonic transducer probe assembly, cannot be angularly rotated relative to the ultrasonic probe assembly and its axis. Meanwhile, the moving coil element of the linear motor which reciprocates along the major axis of the ultrasonic transducer probe assembly is axially asymmetric and is therefore not axially balanced and is consequently prone to rotate. The moving coil is generally confined and guided to prevent unrestrained angular rotation about the probe assembly axis. However, since this moving element must be loosely held in order to allow for its axially reciprocating motion a slight play, and a resultant potential for slight angular rotation, is inevitable. In accordance with the present invention this potential slight angular rotation of the driving element relative to the driven element is accommodated by the linkage. The linkage is preferably a crankshaft employing a joint which will not transmit or couple torque, normally a ball and socket joint, at one of its ends. Nominally this end is at the moving coil element of the linear motor. Furthermore, the coil element normally defines the socket of the joint while the crankshaft terminates in a ball. By this manner of mechanical connection, neither initial angular alignment, nor relative angular movement during operation, between the moving element of the linear motor and the pivoting transducer head is critical to operation of the probe assembly.

In accordance with the third aspect of the present invention an electrically wired connection is made to the transducer head by a wire which is wraped around the pivot shaft of a gimballed cup holding the transducer head. The wire forms a helical coil which connects at one end to the pivoting transducer head and which, at the other end, tangentially vectors from its wrapped position about the pivot shaft to a spatially fixed connection point within the transducer assembly. The relative motion between pivoting and fixed points is accommodated within the turns of the helically wrapped wire. The wire is neither appreciably stressed nor is any significant mechanical moment of force applied to the pivoting transducer head by this manner of electrical connection.

In accordance with the fourth aspect of the present invention, the temperature- and/or pressure-induced volumetric variations in the fluid contained within the ultrasonic probe are accommodated by the inclusion of a compressible element completely within the fluid chamber of the probe. This compressible element is preferably a bladder filled with air, and is preferably in the shape of a cylinder with bellow folds along its surface. The folds allow for distention and extension in the length of the cylinder, and for expansion and contraction in its contained air volume. Since the fluid within the casing is substantially incompressible with temperature changes, the compressible air bladder within the chamber allows chamber pressure to remain substantially constant, preserving uniform ultrasound transmission characteristics, with changes in temperature undergone by the probe.

BRIEF DESCRIPTION IS THE DRAWINGS

These and other aspects of the present invention will become increasing clear with reference to the following drawings and accompanying explanation wherein:

FIG. 1 is a pictorial view showing the preferred embodiment ultrasonic transducer probe assembly in accordance with the present invention.

FIG. 2 is an exploded view, partially in cross section, showing major functional elemements in the ultrasonic trasducer probe assembly in accordance with the present invention.

FIG. 3 is an exploded view particularly showing the air bladder and the electrical connector elements of the ultrasonic transducer probe assembly in accordance with the present invention.

FIG. 4 is a partial cross-sectional view, taken along aspect line 4—4 of FIG. 1, showing the threaded interconnection of the acoustic come to the case of the ultrasonic transducer probe assembly in accordance with the present invention.

FIG. 5 is a pictorial view showing the detailed mechanical connection of a crankshaft to the upper extension of a moving coil within a linear motor assembly within the ultrasonic transducer probe assembly in accordance with the present invention.

FIG. 9 is an exploded perspective view showing an upper member of the linear motor assembly of the ultrasonic transducer probe assembly in accordance with the present invention.

FIG. 10 is an exploded perspective view showing the linear motor assembly of the ultrasonic transducer probe assembly in accordance with the present invention.

FIG. 11 is a detailed perspective view showing the connection of a moving magnet assembly in the region of certain guide portions thereof to a metal sleeve assembly.

DESCRIPTION OF THE PREFERRED EMBODIMENT

Figure 6:
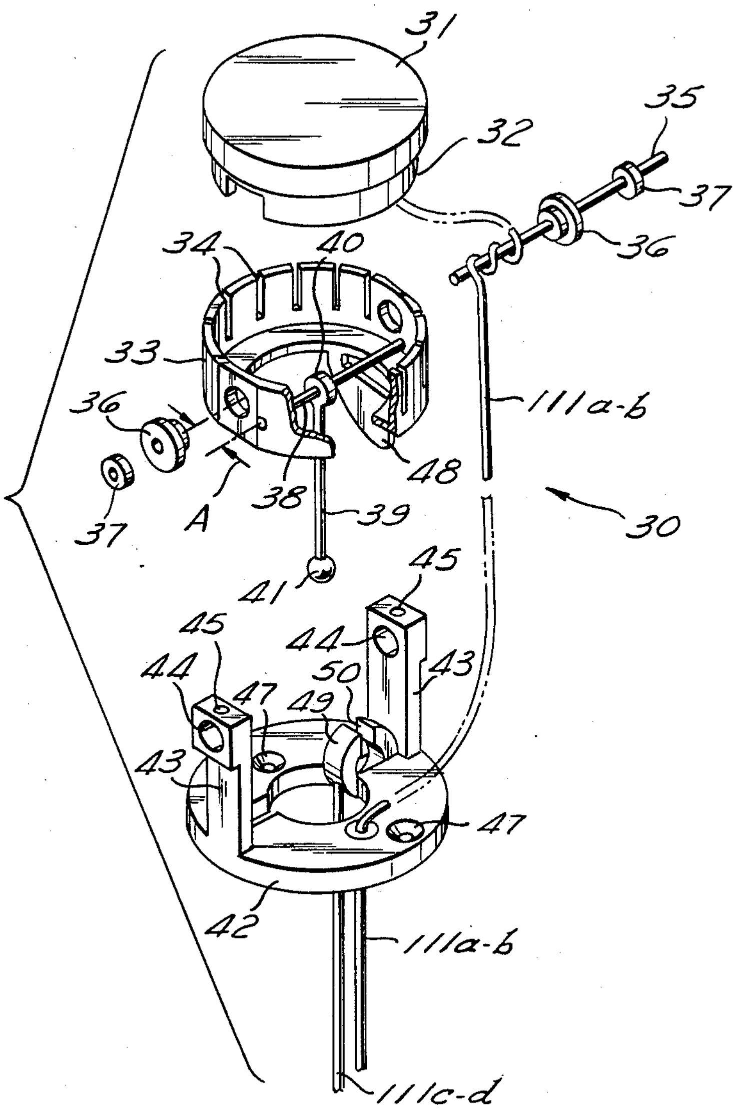
FIG. 6 is an exploded pictorial view showing the transducer mounting assembly element within the ultrasonic transducer probe assembly in accordance with the present invention.

The present invention is embodied within an ultrasonic transducer probe assembly 10 which is shown generally in FIGS. 1–14. Referring first to FIG. 1, an ultrasonic transducer probe 10 constructed in accordance with the principles of the present invention is shown in pictorial view. The probe elements are housed in a case 11, which may be machined from aluminum, or which may be molded of derin, polysulfone or similar material. A lower sleeve 17 at one end of case 11 defines an aperture (not shown) through which cabled connection is made via a cable (not shown) to power supplies, signal generators, and signal processors which are employed in use of the probe for ultrasonic imaging. An acoustic cone or cap 20 is fitted at the end of the case. The cap 20 is made of polyethylene or other material which is highly transmissive to ultrasound. During use, ultrasonic energy passes through the cap 20 to and from an ultrasonic transducer 31 by way of the intervening fluid 22 inside the probe. The fluid 22 is a non-toxic liquid, such as a Siloxane based oil, which acts as both a lubricant and ultrasound couplant. As best seen in FIG. 4, the acoustic cap 20 has interior threads 23 which mate with complementary threads 12 around the periphery of the open end of the case 11, and is sealed in place by a plastic compression band 21. This seal is made fluid-tight by an O-ring 14 which is compressed in groove 13 between the cap 20 and the case 11.

Figure 7:
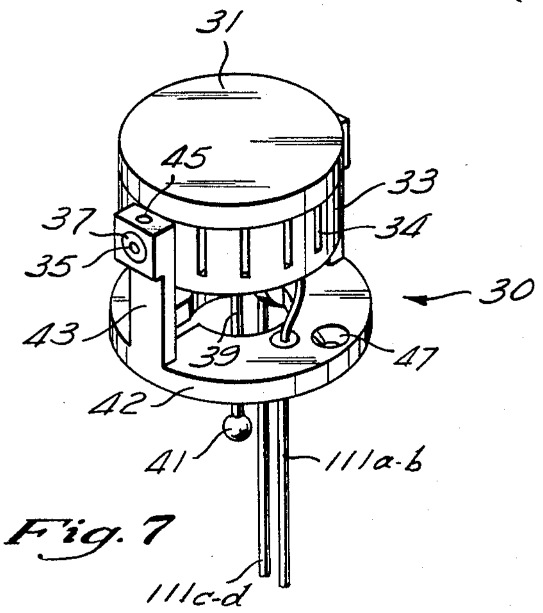
FIG. 7 is an assembled pictorial view of the same transducer mounting assembly element previously seen in exploded view in FIG. 6.
Figure 8:
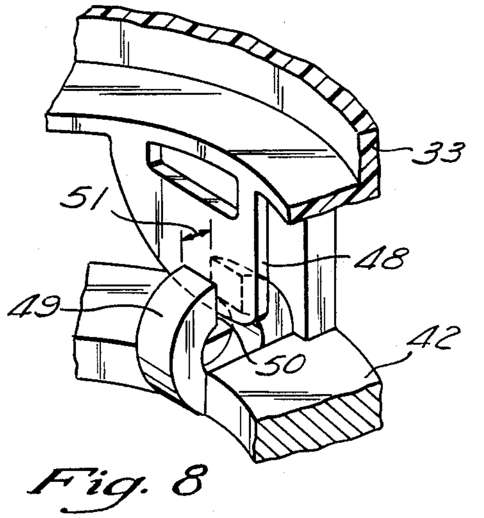
FIG. 8 is a pictorial view showing the detailed structure of a flange upon a transducer cup which flange passes through a gap within a position sensing coil toroidal coil upon a gimbal cup in order that the tilt of the transducer, within the ultrasonic transducer assembly in accordance with the present invention, may be definitively known.
Figure 12:
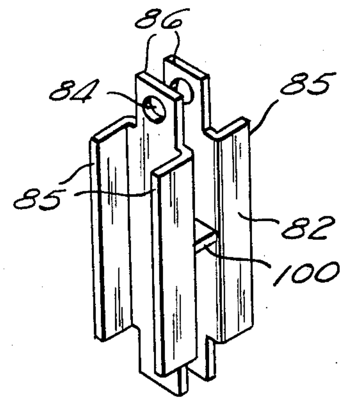
FIG. 12 is a perspective view showing a frame around which coil wire is wrapped to form a moving coil assembly part of the linear motor assembly within the ultrasonic transducer probe assembly in accordance with the present invention.

As may be observed in FIGS. 2, 6, and 7, transducer mounting assembly 30 includes illustrated components 31 through 51. The transducer 31 is seated in a transducer ring 32. The transducer ring 32 then snaps into place in a transducer cup 33. This snapping is facilitated by a slight expansion in transducer cup 33 permited by axial slots 34 therein. This permits incorporating during manufacture a variety of transducers of different characteristics each of which fits transducer rings of the same outer dimension. When a customer orders a probe with a specified transducer, then the selected transducer and ring module can be snapped into the transducer cup and the necessary electrical connections can be made. The transducer cup 33 contains ball bearing fittings 36 on either side, with a hard steel axle pin 35 passing therethrough. A stainless steel crank pin 38 is press fit through the transducer cup 33 parallel to the axle pin 35. In a preferred embodiment of the present invention, the crank pin 38 is spaced apart from the axle pin 35 by a distance A of approximately 0.090 inches. This nominal spacing is one of the determining factors of the angle through which the transducer 31 is pivoted. In the preferred embodiment, the oscillation angle is 90 degrees. A one thousandth of an inch variation in the spacing distance corresponds to approximately a one degree variation in the oscillation angle.

As may be best observed in FIG. 6, one end of the crankshaft 39 is connected to the crank pin 38 in a bearing 40. The other end of the crankshaft 39 is connected to the moving coil assembly 80 of the linear motor assembly 60 in a ball and socket joint. This joint, shown in detail in FIG. 5, consists of the ball 41 at the end of crankshaft 39 (observable in FIG. 6) and the socket defined by holes 84 at the upper extension 86 to coil assembly 81 of moving coil assembly 80 (observable in FIGS. 9 and 10). This construction, further discussed in conjunction with FIGS. 9 and 10, is one of the significant aspects of the present invention. Particularly, the crankshaft 39 will not transmit torque, or angular motion, between the moving coil assembly 80 and the linear motor assembly 60 which it connects. In the preferred embodiment this is because of the ball and socket joint, which joint could have equally as well been located at the other end of crankshaft 39. Alternatively, it should be recognized that crankshaft 39 could itself incorporate a rotary joint. Alternatively, other means well known in the art (such as hydraulics) for transmitting axial force without torque could have been used to couple the driving member of moving coil assembly 80 to the driven member of transducer 31.

Continuing in FIG. 6, the ends of the axle pin 35 which extend from the transducer cup 33 are located in bearings 37 in holes 44 in arms 43 which extend from the base of a gimbal cup 42. The bearings 37 are held firmly in the holes 44 in the gimbal cup arms 43 by orthogonally directed set screws 45 in the gimbal cup arms 43. Referencing FIG. 2, the gimbal cup 42 is held in place in the case 11 by screws 46, which pass through holes 47 in the gimbal cup 42 and into threaded holes 15 in the case 11. The base of the gimbal cup 42 fits against the upper plug 70 to the linear motor assembly 60.

The complete transducer mounting assembly 30 is illustrated in FIG. 7. In accordance with the present invention, the transducer mounting assembly 30 is capable of providing a sensor output which is indicative of the precise instantaneous angle that transducer 31 is tilted about pivot shaft 35. This sensor output is obtained from position-sensing toroidal coil 49, shown in FIG. 6 and further in expanded view in FIG. 8. The toroidal coil 49 is affixed within slot 50 within the base of the gimbal cup 42. The gap 51 of this toroidal coil 49 is variably entered by flange 48 of the transducer cup 33 dependent upon how much this transducer cup 33, and the transducer 31 mounted therein, are tilted about the axis defined by pivot shaft 35. The contours of flange 48 are such that a variable amount of metal, nominally a ferrous metal, will be rotated ie pass within the gap 51 of toroidal coil 49 in response to a corresponding variable tilt angle of the transducer 31. This amount of metal changes the inductance of toroidal coil 49 in a manner which may be sensed by interconnected electronics circuitry (not shown). Accordingly, the toroidal coil 49 which is variably entered in its gap 51 by flange 48 consitutes a sensor of the angular tilt of transducer 31.

The linear motor 50 which is shown to be located within case 11 in FIG. 1 is further shown in exploded view in FIG. 10. The linear motor 60 includes illustrated components 61–96. An upper plug 70 is press fitted to the top of composite metal sleeve assembly 61 so that guide ridge 71 fits into radial guide slot 73. Likewise, lower plug 72 is press fitted to the bottom of sleeve assembly 61 so that guide ridge 74 fits into radial guide slot 75. Between the upper plug 70 and the lower plug 72 and within the sleeve assembly 61 is an upper compression spring 65, a motor subassembly 80 and a lower compression spring 67. The motor subassembly 80 includes permanent magnets 87, moving armature coil 81, and those miscellaneous parts which are all illustrated in exploded view in FIG. 9. The permanent magnets 87 are secured to sleeve assembly 61 by machine screws 91 which slip both holes 63 in sleeve 61 and holes 90 in the permanent magnets 87 in order to threadingly engage backing plates 89 to which the magnets 87 are permanently affixed. While the magnets 87 remain fixed to sleeve 61, the remaining parts of motor subassembly 80 (shown in FIG. 9) slide axially in sleeve 61.

Figure 14:
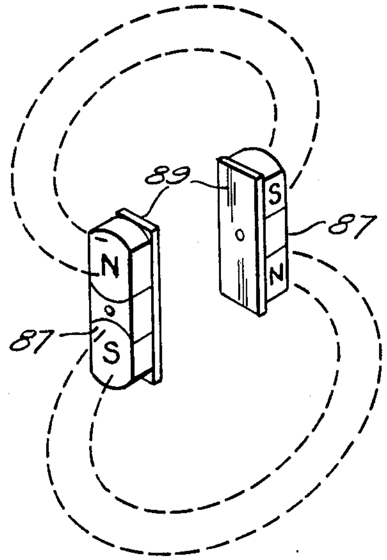
FIG. 14 is a diagrammatic representation showing the field lines of magnetic flux created by the opposed permanent magnets within the linear motor assembly which is part of the ultrasonic transducer probe assembly in accordance with the present invention.

Referencing FIG. 9, the motor subassembly 86 includes moving armature coil 81. A coil of wire 83 is wrapped about an H-frame 82 which is illustrated in isolation in FIG. 12. The wire coil 83 is substantially in a plane which is defined bby and which is perpendicular to the plane of the center portion 100 of H-frame 82. It may be observed in FIG. 9 that this plane is orthogonal to a straight line between oppositely disposed magnets 87. The North, or "N", and South, or "S", poles of the two magnets 87 are in opposite orientation as illustrated in FIG. 14. Consequently, the lines of magnetic force, or flux, between the magnets 87 are substantially as illustrated in FIG. 14. The plane of moving armature coil 81, and particularly of wire coil 83 therein, may be observed to be substantially orthogonal to the field lines of magnetic flux between the permanent magnets 87.

Continuing in FIG. 9, the "H" frame 82 includes a pair of guide flanges 85. These guide flanges 82 are oriented as partial chords to the circular cross-section of bore 62 to sleeve 61 (shown in FIG. 10). The guide flanges 85 define U-channels within which the magnets 87 and the magnets' backing plates 89 will slide without substantial contact. A substantially central position of moving armature coil 81 within motor subassembly 80 and within the entire linear motor 60 is established by (i) the substantially equal displacement of end guides 92 respectively from upper plug 70 and lower plug 72 by (ii) action of substantially equal strength springs 65 and 67 (all shown in FIG. 10). The frame 82 further has upper extension 86 defining holes 84. The extensions, including upper extension 86, of coil frame 82 pass through the substantially square apertures 93 of the end guides 92. These end guides 92 are made of an insulating plastic which exhibits low frictional resistance to sliding within the internal bore 62 of sleeve 61. The end guides 92 are prevented from rotating within sleeve 61 by their guide tabs 94 which engage the complementary structure of guide ridge 64 on the interior of sleeve 61, all as shown in partial cross-sectional view in FIG. 11.

Figure 13:
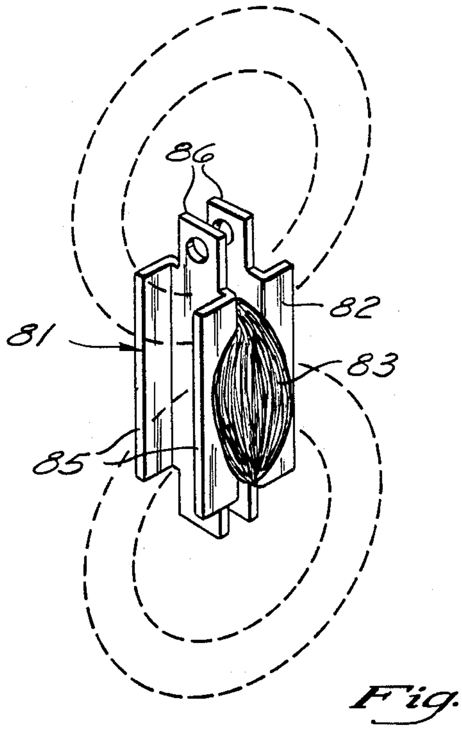
FIG. 13 is a diagrammatic representation showing the field lines of magnetic flux emanating from an energized moving coil assembly within the linear motor assembly which is part of the ultrasonic transducer probe assembly in accordance with the present invention.

When the wire coil 83 is electrically energized, through a wired connection as will be explained, it produces magnetic field which is diagrammatically illustrated in FIG. 13. The direction of magnetic flux within this magnetic field is, of course, dependent upon the direction of a current flow which is induced by a voltage of a corresponding polarity within coil 83. It may be noted that the lines of magnetic flux resultant from energization of coil 83 are similar to, and substantially coincident with, the lines of magnetic flux resultant from permanent magnets 87. This means that the flux coupling is optimal or nearly optimal, and that the linear motor 60 is efficient. Referring to FIGS. 9 and 10, the electrical energization of coil 83 will cause movement of the moving armature coil 81, coil frame 82, and end guides 92 axially within sleeve 61 and against the spring forces of springs 65 and 66. The direction of movement of motor subassembly 80, and which one of the springs 65, 67 compresses and which one extends, will be determined by the direction of current flow within coil 83.

Connection between the linear motor 60, specifically in the motor subassembly 80 and more specifically in the holes 85 of coil frame 82 (shown in FIGS. 9 and 10), and the pivotable transducer mounting assembly 30 specifically at the crank pin 38 (shown in FIG. 6) is made by crankshaft 39 (shown in FIGS. 2, 5, 6, and 7). The crankshaft 39 is affixed for rotation about crank pin 38 by bearing 40, as previously explained during discussion of FIG. 6. The other end of crankshaft 39 terminates in ball 41. This end of crankshaft 39, and its ball 41, pass through the central aperture of upper plug 70 (shown in FIG. 9). The ball 41 is retained between the holes 84 to upper extension 86 to coil frame 82, as is shown in detail side view in FIG. 5. This second end connection of crankshaft 39 is thus by a ball and socket joint.

Also as previously explained during discussion of FIG. 6, this connection of crankshaft 39 in a manner which will not transmit torque is one of the significant aspects of the present invention. Particularly, the ball and socket joint can accomodate both angular misalignment and angular variation between the pivotable transducer mounting assembly 30 and the motor assembly 80 of the linear motor 60. These variations cannot be well tolerated by a crankshaft which is pinned at both ends. It has been found that the angular alignment of crank pin 38 and of motor subassembly 80 relative to the axis of case 11 is difficult to initially establish during assembly, and to maintain during operation. In this regard, it should be noticed that end guides 92 must slide freely within sleeve 61 which is affixed to case 11. Consequently the motor subassembly 80, and the extension 86 to the coil frame 82 therein, should be expected to twist, or rotate, very slightly in a random manner during operation. Although the pivotable transducer may be initially aligned to the linear motor, and although a rudimentary alignment is thereafter maintained, careful consideration of the forces acting on crankshaft 39, bearing 40 and crank pin 38 (which should and do exhibit low mass as reciprocating components) will reveal that axial forces only should be coupled by the crankshaft 39. The coupling of torque should be avoided within the crankshaft 39 or at the pinned ends thereof (such as at bearing fit 40). Transmission of axial forces while avoiding coupling of rotational forces is accomplished by the ball and socket joint. This joint could obviously be alternatively positioned at the transducer mounting assembly 30 end to crankshaft 39, or the joint could be replicated at both ends of crankshaft 39. Alternatively, the crankshaft itself could incorporate a rotary slip joint.

The electrical connections of the transducer are facilitated in part by the cable **111*a–b* shown in FIGS. 2, 3, and 6 which is preferrably of the coaxial type. Each of the two conducts within this cable 111*a–b* make a first end electrical connection, preferably by soldering, at the transducer 31. As may be best observed in FIG. 6, this cable 111 *a–b* is wound around pivot shaft 35, forming a toroidal coil of several turns about the shaft. The cable 111*a–b* vectors off at a tangent to this toroidal winding in order to connect to the transducer 31 at a first end, or to be routed further into case 11 before exiting probe 10 at a second end. Inspection of this preferred manner of electrical connection via a coil about the pivot shaft, which manner of connection is shown in FIG. 6, will reveal that the tilting, or pivoting, of the transducer 31 about pivot shaft 35 results in a slight tensioning, or slight loosening, of the turns of the coiled cable 111*a–b*. Any undesireable counteracting torque on the pivoting of transducer 31, or any sudden releases of energy resulting in erratic angular movement and/or minute vibrations to the transducer 31, or any appreciable flexing or wearing of cable 111*a–b*** are almost entirely avoided by the preferred manner of its connection. This electrical connection is but part of that particular aspect of the present invention which is concerned with improved electrical routing and wired connections within an ultrasonic transducer probe.

Continuing with the electrical connections within probe 10, the cable **111*c–d* shown in FIGS. 6 and 7 is nominally the extension of two wires, nominally wrapped as a twisted pair, from the two terminals of toroidal coil 49. Both the cable 111*a–b* and the cable 111*c–d*, totaling four electrical paths, are routed through the circumferential notch 77 in upper plug 70, within the axial channel 76 of sleeve 61, through the circumferential notch 78 of lower plug 72 (all shown in FIG. 10) and along the outside of air bladder 100 (shown in FIGS. 2 and 3) to terminate in connector 110 (shown in FIG. 3**).

Electrical connections to coil 83 within moving armature coil assembly 81 within motor subassembly 80 are made via the springs 65, 67 which further serve to mechanically bias the movement of motor subassembly 80. Particularly, the upper spring 65 has a lower tail 66 which fits through hole 95 in the upper one of end guides 92 and thereafter connects, as a first electrical connection, to coil 83. The other end of upper spring 65 is connected, nominally by soldering, to wire **111*c*. This wire 111*c* is shown isolated from nearby wires 111*a–d*** in FIG. 7 in order that its individual routing within axial groove 76 of sleeve 61 may be more clearly observed. The lower spring 67 has an upper tail 68 which fits through hole 96 in the lower one of end guides 92 and thereafter connects, as a second electrical connection, to coil 83. The lower spring 67 also has a lower tail 69 which fits through hole 79 in lower plug 72, and thereafter is connected, nominally by soldering, to wire 111*f* which is shown in FIG. 2. This electrical connection to a moving coil element of a linear motor through the same springs which mechanically bias movement of the coil is another part of that aspect of the present invention which is concerned with improved electrical routing and wired connections in an ultrasonic transducer probe.

The cables 111*a–f* all extend to a point within case 11 adjacent the lower extremity of linear motor 60. Beyond this point these cables 111*a–f* are routed along the outside of air bladder 100 and are soldered to six of the seven through-pins 112*a–g* of connector body 110. The connector body 110 is watertight and its pins 112*a–g* are potted. It is normally of the male type, and connects to a cable (not shown) which supplies power and signal drive to, and which receives sensor outputs from, probe assembly 10.

The watertight connector body 110 has a flange 113 which engages a like feature within the central bore of lower collar 17. Between these mating surfaces is positioned an O-ring 102. When the lower collar 17 is threaded onto case 11 by the engagement of interior threads 18 with exterior threads 16, then the O-ring 102 is compressed and the entire probe assembly 10 is sealed. Tightening of the lower collar 17 to effect this seal may be aided by fitting a wrench to flat 19. The entire inside of the probe 10 from cone, or cap, 20 to connector body 110 is preferably filled with an incompressible fluid save for air bladder 100. The fluid does not interface with motion of the liner motor, nor with any electrical paths.

The air bladder 100 contains a sealed quantity of a compressible gas, preferably air and located within the fluid reservoir defined within probe 10. The air bladder 100 is preferably in the shape of a cylinder, as illustrated, which preferably exhibits bellows folds or pleats or, alternatively, alternating grooves and ridges circumferentially along its surface. The fluid within the reservoir of probe 10 expands with increasing temperature and contracts with decreasing temperature. Save for the compressible air bladder 100 this expandion and contraction could cause leakage within the instrument.

Fluid leakage is particularly undesirable because, as the fluid 22 leaks out, the fluid is replaced by air when the pressure within the probe 10 equalizes to outside atmospheric pressure. Once in the fluid compartment of probe 10, the air bubbles soon make their way to that upper region of the compartment where ultrasonic transducer 31 is located. When the air bubbles are located in front of the face of the ultrasonic transducer 31 then they cause problems because ultrasound energy is attenuated and scattered by air. The presence of air bubbles can thereby render the transducer probe virtually useless for diagnostic imaging.

A particularly troublesome source of fluid leakage and bubble formation is resultant from a thermal cycling of the probe 10. As the probe 10 is warmed the fluid 22 will expand in accordance with its temperature expansion coefficient. The pressure within the fluid compartment will build and some fluid may leak out. When the probe 10 is thereafter cooled, the fluid will contract, which creates a negative pressure in the compartment relative to atmospheric pressure until air leaks in to equalize the pressure. Such thermal cycling may occur, for instance, when a probe is left in the trunk of a car on a warm day, and is then taken into an air-conditioned building.

To account for the effects of thermal cycling, the preferred embodiment probe 10 in accordance with the present invention incorporates the air bladder 100 as an expansion chamber. The expansion chamber is a compressible part of the fluid compartment. The bellows-fold wall of the air bladder 10 expansion chamber is extensible and contractable in length, thereby readily allowing the volume of air within air bladder 100 to expand or contract. As the fluid expands and contracts, the air bladder 100 will correspondingly contract and expand to maintain the desired fluid pressure within the compartment as the fluid volume changes. Desirably, the air bladder 100 expansion chamber is at least one-fifth as large as the total fluid volume within probe 10 in order to accommodate wide variations in the fluid volume. An adequately large expansion chamber will respond to fluid volume changes with relatively little distension or contraction of the chamber. However, the desireability of a large expansion chamber runs counter to favored design characteristics of the probe itself, which are that the probe should be made as small and light as possible.

In accordance with one aspect of the present invention, an expansion chamber for an ultrasonic transducer probe is provided which is large enough to accommodate large variations in fluid volume while at the same time being arranged to permit a compact probe design. This is accomplished by emplacing the air bladder 100 expansion chamber completely within the fluid chamber of the probe. Unlike prior art expansion chambers, there is no wasted space resulting from the use of a separate volume of the probe solely for the expansion chamber. Neither is a one wall of the expansion chamber outside the fluid chamber of the probe and connecting to the atmosphere. The volume encompassed by the air bladder 100 expansion chamber provides the benefit of accommodating significant temperature changes without causing any change in the exterior volume or overall dimensions of the probe 10.

In accordance with the preceding discussion, the present invention will be seen to have seperate and severable aspects relating to a mechanical linkage for coupling a reciprocating element of a linear motor to a pivoting transducer head, an improved linear motor employing a coil as reciprocating element, an improved electrical connection to a pivotable transducer head, an improved electrical connection to a reciprocating coil element within a linear motor, an imporved air bladded entirely within the fluid chamber of an ultrasonic probe, and other aspects. These aspects are readily susceptible of modification and/or recombination by a practioner in the art of acousto-mechanical systems. For example, once it is realized that the temperature-compensating cylindrical air bladder may be entirely within the fluid chamber, and once it is considered that the cylinderical linear motor is also within the air chamber, then an attempt can be made to integrate the structures of the cylindrical linear motor and cylindrical air bladder. For example, this integration might be accomplished essentially by sealing air-tight the cylindrical linear motor, thereby allowing for its volumetric change, while still communicating electrical energy and mechanical force, particularly by using membranes or the like. Therefore, the following claims should be interpreted broadly in accordance with their language, only, and not solely in accordance with that preferred embodiment ultrasonic transducer probe apparatus within which the diverse aspects of the present invention have been taught.

We claim:

1. In an ultrasonic transducer probe assembly having a transducer mechanically actuable for pivoting and a linear motor imparting linear reciprocating motion, an improvement to the mechanical linkage by which a reciprocating element of the linear motor imparts pivoting motion to the transducer, the improved mechanical linkage comprising:

a crankshaft, extending between a point of connection to the reciprocating element of the linear motor and a point of connection to the pivotable transducer located off a pivot axis thereof, in order that a linear reciprocating force of the element may be axially transmitted along the crankshaft to impart pivoting motion to the transducer said crankshaft including means for allowing three dimensional motion of said crankshaft with respect to at least one of said points of connection, whereby the crankshaft is incapable of transmitting torque between the reciprocating element and the pivotable transducer.

2. The ultrasonic transducer probe assembly improved mechanical linkage according to claim 1 wherein said means for allowing three dimensional motion:

a ball and socket joint positioned on at least one of the points of connection capable of transmitting axial force to the crankshaft.

3. The ultrasonic transducer probe assembly improved mechanical linkage according to claim 2 wherein the ball and socket joint is at the point of the connection of the crankshaft to the reciprocating element at the linear motor.

4. The ultrasonic transducer probe assembly improved mechanical linkage according to claim 3 wherein the ball is upon the crankshaft and the socket is upon the reciprocating element of the linear motor.

5. The ultrasonic transducer probe assembly improved mechanical linkage according to claim 1 wherein the reciprocating element of the linear motor comprises:

an electrical coil.

6. A method of transmitting force within an ultrasonic transducer probe assembly between a reciprocating element of a linear motor and a pivotable transducer which is driven by the reciprocating element for pivoting motion, the method of force transmission comprising:

connecting a crankshaft, between a point upon the reciprocating element and a point upon the pivotable transducer which is displaced from a pivot axis thereof, in a manner which allows three dimensional motion of said crankshaft with respect to at least one of said points of connection so that the axial force is communicated along the crankshaft from the reciprocating element to the pivotable transducer in order to drive the transducer in pivoting motion but also effectively isolating the crankshaft from the effects of torque.

7. The force transmission method according to claim 6 wherein the connecting of at least one of the points is by a ball and socket joint.

* * * * *